United States Patent [19]

Orgill et al.

[11] Patent Number: 5,716,411
[45] Date of Patent: Feb. 10, 1998

[54] METHOD OF SKIN REGENERATION USING A COLLAGEN-GLYCOSAMINOGLYCAN MATRIX AND CULTURED EPITHELIAL AUTOGRAFT

[75] Inventors: Dennis P. Orgill, Belmont; Charles E. Butler, Brookline; Mark Barlow, Boston; Scott Ritterbush, Saugus; Ioannis V. Yannas, Newton; Carolyn C. Compton, Chestnut Hill, all of Mass.

[73] Assignees: Brigham & Womens Hospital, Boston; Massachusetts Institute of Technology, Cambridge, both of Mass.; Shriners Hospitals for Crippled Children, Tampa, Fla.

[21] Appl. No.: 596,060

[22] Filed: Feb. 6, 1996

Related U.S. Application Data

[63] Continuation of Ser. No. 229,732, Apr. 19, 1994, Pat. No. 5,489,304.
[51] Int. Cl.$^6$ .................................................. A61F 2/10
[52] U.S. Cl. .................... 623/15; 435/371; 435/360; 424/426
[58] Field of Search .................... 623/11, 15, 16, 623/66; 128/DIG. 8, 898; 435/240.2, 240.21, 240.23, 360, 326, 371; 424/422, 426

[56] References Cited

U.S. PATENT DOCUMENTS

| | | | |
|---|---|---|---|
| 4,060,081 | 11/1977 | Yannas et al. | 128/156 |
| 4,280,954 | 7/1981 | Yannas et al. | 260/123.7 |
| 4,505,266 | 3/1985 | Yannas et al. | 128/1 R |
| 4,888,291 | 12/1989 | Barrandon et al. | 435/240.241 |
| 5,282,859 | 2/1994 | Eisenberg | 623/11 |
| 5,334,527 | 8/1994 | Brysk | 435/240 |
| 5,489,304 | 2/1996 | Orgill et al. | 623/15 |

OTHER PUBLICATIONS

Mulligan, "The Basic Science of Gene Therapy" Science 260:926–932, May 1993.

Hodgson, "The Vector Void in Gene Therapy" Bio/Technology 13:222–225, Mar. 1995.

Etienne–Julan, "The efficiency of cell targeting by recombinant retroviruses depends on the nature of the receptor and the composition of the artificial cell–virus linker" Journal of General Virology 73:3251–3255, 1992.

T. Kangesu, et al., "A Porcine Model Using Skin Graft Chambers for Studied on Cultured Keratinocytes," British Journal of Plastic Surgery, 46:393–400 (1993).

N. Carver et al., "Restoration of Basement Membrane Structure in Pigs Following Keratinocyte Autografting," British Journal of Plastic Surgery, 46:384–392 (1993).

T. Kangesu, et al., "Kerato–dermal Grafts: The Importance of Dermis for the in vivo Growth of Cultured Keratinocytes," British Journal of Plastic Surgery, 46:401–409 (1993).

Bell et al., "Living Tissue Formed in vitro and Accepted as Skin–Equivalent Tissue of Full Thickness," Science, 211:1052–1054 (1981).

Primary Examiner—Robert A. Clarke
Attorney, Agent, or Firm—Hamilton,Brook,Smith & Reynolds, P.C.

[57] ABSTRACT

The present invention relates to a method of skin regeneration of a wound or burn in an animal or human. This method comprises the steps of initially covering the wound with a collagen glycosaminoglycan matrix, allowing infiltration of the grafted GC matrix by mesenchymal cells and blood vessels from healthy underlying tissue and applying a cultured epithelial autograft sheet grown from epidermal cells taken from the animal or human at a wound free site on the animal's or human's body surface. The resulting graft has excellent take rates and has the appearance, growth, maturation and differentiation of normal skin.

7 Claims, 1 Drawing Sheet

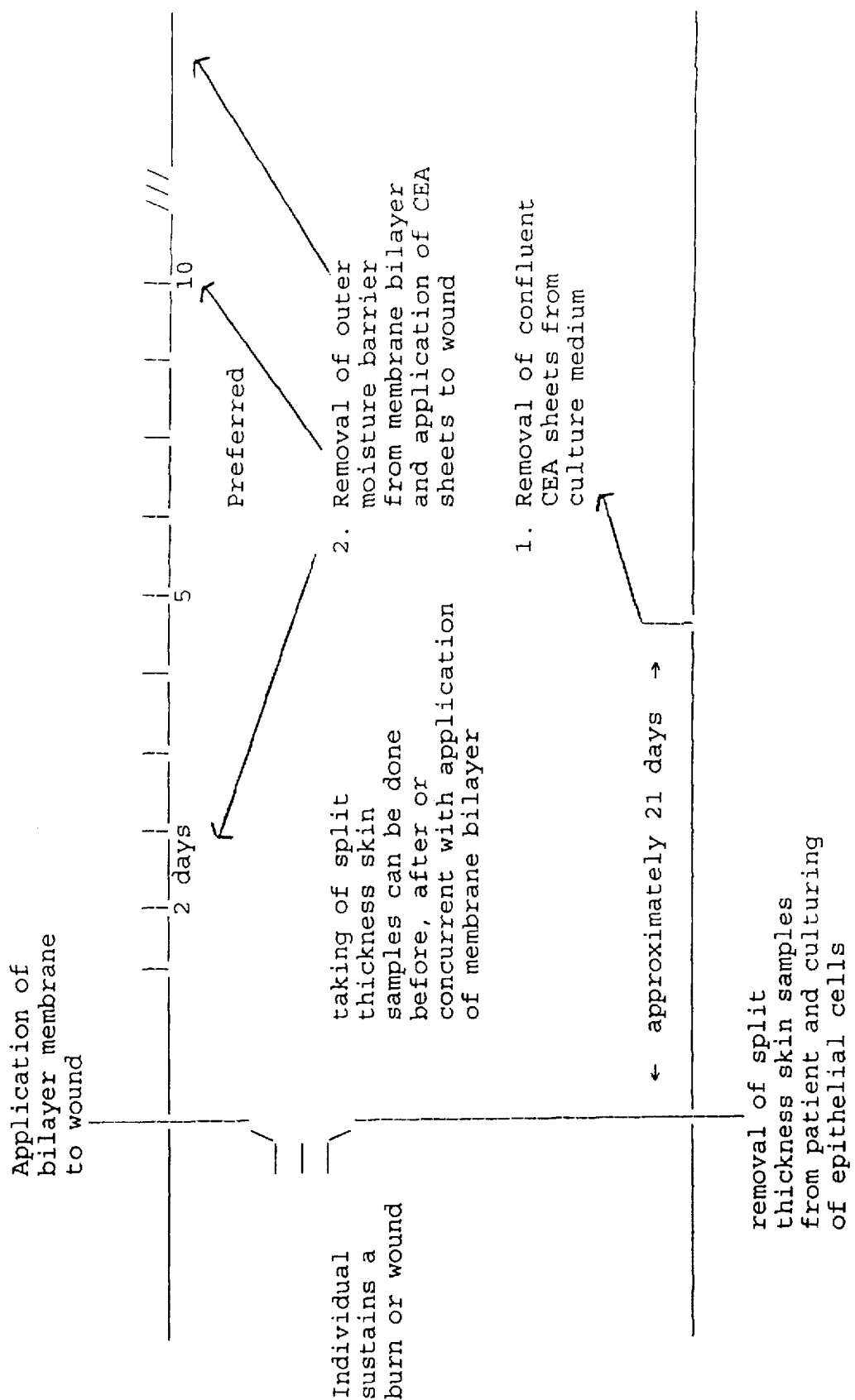

METHOD OF SKIN REGENERATION USING A COLLAGEN-GLYCOSAMINOGLYCAN MATRIX AND CULTURED EPITHELIAL AUTOGRAFT

This application is a continuation of application Ser. No. 08/229,732 filed Apr. 19, 1994, now U.S. Pat. No. 5,489,304, which is incorporated herein by reference in its entirety.

Government Support

The research described herein was supported in part by grant number GMO-7560-17 from the National Institutes of Health. The government has certain rights in this invention.

BACKGROUND ART

A patient who has suffered extensive skin loss or injury is immediately threatened by infection and by excessive loss of fluids. To meet both of these needs, a large skin wound must be closed promptly by some type of membrane. The most direct method of accomplishing this purpose is by transplanting partial-thickness sections of skin to the wound, thereby sealing the wound and preventing fluid loss and infection.

The transplanted section of skin can be removed ("harvested") from an animal of another species. This type of transplant is referred to as a xenograft. However, a xenograft suffers from the disadvantage that the transplanted skin is rejected and can only serve to cover the wound for three to five days. Consequently, a xenograft can only serve as a stopgap while the patient's skin slowly heals.

The transplanted section of skin can also be harvested from human cadavers. This type of transplant is referred to as an allograft or homograft. However, cadaveric skin is in short supply, and allografts are often, like xenografts, rejected. Although immunosuppressive drugs can increase the period of time which an allograft may cover a wound, they also leave the patient vulnerable to infection. Allografts also suffer from the disadvantage that they expose the patient to the risk of transmission of diseases such as hepatitis and AIDS.

The most desirable form of transplant is an autograft, in which skin from an undamaged area of the patient or identical twin is harvested and used to cover the wound. The risk of rejection and disease transmission is thereby eliminated, and the transplanted skin proliferates to form a new layer of dermis and epidermis.

The harvesting operation is a painful, invasive process, which causes scarring. It should therefore be kept to a minimum. In addition, a severely burned patient may suffer skin loss or damage on nearly all of his or her body. This may severely limit the amount of healthy, intact skin that is available for autografting. When this occurs, xenografts or homografts may be placed across the entire wound surface to control infection and dehydration; they are gradually replaced as autografts become available. Autografts may be harvested repeatedly from a donor site. In such an operation, an area of xenograft or homograft is removed and discarded, and replaced by an autograft. Each donor site must be allowed to heal before another autograft is removed from it; this requires a substantial delay, and prolongs the recovery of the patient. Furthermore, the quality of the skin graft diminishes with each successive harvest.

Consequently, much effort has been spent to create a skin substitute for the massively burned patient with limited donor sites. Attempts have been made to manufacture artificial skin from both biologic and synthetic materials with variable results. An acceptable skin substitute should provide both the components and functional results of normal skin. Two important components of the skin are the epidermis and dermis. The epidermis is the outer layer of skin. It consists of cells at various stages of differentiation and maturity. Basal cells are located at the lowest level (adjacent to the dermis) and are the least differentiated. The dermis is located below the epidermis and comprises mesenchymal cells and blood vessels. The junction between the dermis and epidermis is referred to as the basement membrane and is responsible for one of the most important functional results of normal skin, namely the tight adhesion of the dermis to the epidermis. This tight adhesion adds strength and durability to the skin and prevents "shearing" of the epidermis. "Shearing" is the "rubbing off" of the epidermis when lateral forces are applied to the skin, and can result in blistering and skin fragility.

One of the most promising skin substitutes is a synthetic bilayer membrane (hereinafter collectively referred to as "CG bilayer"). This membrane comprises a bottom layer (hereinafter referred to as "CG matrix") which is a highly porous lattice made of collagen and glycosaminoglycan. The outer layer is a membrane semipermeable to moisture and impermeable to infectious agents such as bacteria. The CG lattice serves as a supporting or scaffolding structure into which blood vessels and mesenchymal cells migrate from below the wound, a process referred to as "infiltration". Infiltration is responsible for creating a new dermis, referred to as the "neodermis", which replaces the CG matrix as it biodegrades. Epithelial cells from undamaged skin surrounding the edges of the wound migrate into CG matrix to create a new epidermis, referred as the "neoepidermis". Because burns and other skin wounds tend to be shallow, mesenchymal cells need not migrate very far to create a neodermis. However, burns often cover large areas of a patient's body surface. Consequently, epithelial cells often must migrate great distances to adequately close a wound. As a result, thin skin grafts are required to close the wound. Consequently, a need exists for new procedures which can hasten the coverage of the CG matrix with a neoepidermal layer.

A second promising technology for manufacturing and applying artificial skin is referred to as cultured epithelial autograft (hereinafter referred to as "CEA"). In this method split thickness skin samples are harvested from a site on the patient's body surface that is wound free. The epithelial cells from this graft are grown in culture to give epithelial sheets that are applied directly to the wound bed, basal side down.

The CEA method suffers from the limitation that it only applies a neoepidermis to the wound bed. There is no dermis or basement membrane present at the time of application, and, therefore, no basement membrane. Thus, there is nothing to secure the neoepidermis to the underlying tissue, resulting in poor take rates for CEA sheets applied directly onto wound beds. This is evidenced by shearing and blistering of the transplanted CEA. Consequently, efforts have been made to use dermal substrates, such as cadaveric skin to improve take rates. However, allograft rejection, the risk of disease transmission and limited availability of cadaveric skin are serious limitations on the usefulness of this technique.

Despite the promise of CEA as a technique for treating wounds, improvements are needed if this technique is to adequately meet the needs of patients with wounds covering large portions of their bodies. Take rates need to be improved without incurring the limitations and risks involved in using cadaveric skin. Furthermore, a patient's wounds must either be exposed or temporarily covered during the approximately three week period during which the CEA sheets are being grown.

SUMMARY OF THE INVENTION

The present invention pertains to a method for regenerating skin at a burn or wound on a human or animal which comprises the steps of applying a coliagen-glycosaminoglycan matrix (CG matrix) having an outer moisture barrier (e.g. a silicone layer) to a wound so that the semipermeable moisture barrier is exposed to the air. Blood vessels and mesenchymal cells are allowed to infiltrate the CG matrix from tissue beneath the CG matrix, after which the moisture barrier on the CG matrix is replaced with a cultured epithelial autograft (CEA) sheet. This CEA sheet is produced by harvesting split-thickness skin samples from an area of the human or animal's body surface that is wound free and culturing the epithelial cells from the split thickness skin samples until the cultured cells have reached confluence. Over time a neodermis and neoepidermis are formed at the burn or wound site, resulting in tissue having the appearance, differentiation and growth of normal skin.

The present invention has many advantages. It allows immediate wound coverage, provides excellent CEA take rates and produces a result similar to native skin. Preparation of CEA sheets requires only that a minimal amount of skin be harvested from the patient, thereby reducing the discomfort to the patient. CG bilayers are completely synthetic and biodegradable over time. There is therefore no risk of disease transmission from donor to patient. In addition, collagen glycosaminoglycan can be manufactured in bulk and stored for extended periods of time.

DESCRIPTION OF THE FIGURE

The Figure is a time course showing the sequence of steps in the present invention.

DETAILED DESCRIPTION OF THE INVENTION

The present invention refers to a method of skin regeneration for burns or wounds on a human or animal. This invention overcomes many of the shortcomings presented by methods presently used to regenerate skin to cover burns or wounds. The bottom layer is initially a bi-layer comprising a highly porous lattice that is covered with an outer membrane that is a moisture barrier. The wound is covered by this bottom layer, with the lattice applied directly to the wound and with the moisture barrier exposed to the air.

The lattice serves as a temporary substitute for the dermis and can be any structure that has the following characteristic: the composition and structure of the lattice must be such that is does not provoke a substantial immune response from the graft recipient. The lattice must be sufficiently porous to permit blood vessels and mesenchymal cells from healthy tissue below the wound to migrate into the lattice. As discussed hereinabove, this migration is referred to as "infiltration" and is responsible for the generation of the neodermis. To facilitate the formation of the neodermis, the lattice is biodegradable. This biodegradation must not proceed so rapidly that the lattice disappears before sufficient healing occurs, i.e. before sufficient neodermis forms. Lattices that degrade too slowly impede cell migration and cause the formation of a fibrotic layer of cells surrounding the lattice. A lattice which biodegrades after about thirty days is preferable.

The moisture barrier is any composition which can serve as an outer surface to the lattice and must be capable of being manually removed at will from the lattice when the CEA sheets are to be applied to the wound, as described hereinbelow. Compositions suitable for use as a moisture barrier must also have the property of being semipermeable to the passage through the wound of fluids from inside the body and impermeable to microorganisms such as bacteria and viruses from outside the body. The moisture barrier also imparts several desirable physical properties to the bi-layer such as tensile strength and suturability.

A preferred embodiment of the present invention employs a highly porous lattice comprised of collagen and glycosaminoglycan (referred to hereinafter as "GAG"), i.e. a collagen glycosaminoglycan matrix (referred to hereinafter as "CG matrix") with a silicone elastomer as the outer membrane. A CG matrix with an outer silicone surface is prepared according to methods known to those skilled in the art. See U.S. Pat. Nos. 4,060,081 (Yannas et al., 1977), 4,280,954 (Yannas et al., 1981) and 4,505,266 (Yannas and Burke, 1985), the teachings of which are incorporated herein in their entirety. Various forms of GAG which may be suitable for use in this material include chondroitin 6-sulfate, chondroitin 4-sulfate, heparin, heparin sulfate, keratan sulfate, dermatan sulfate, chitin and chitosan.

It is possible to control several parameters of the CG matrix (primarily crosslinking density, porosity and GAG content) to control the rate of biodegradation of the lattice. Specific conditions for forming a CG matrix suitable for use in the present invention are given in the Exemplification. However, the skilled artisan will know of other conditions for forming CG matrices with variations of the above-mentioned parameters which are similarly suitable for use in the present invention. In addition, certain applications of skin regeneration may require matrices which degrade more slowly or more quickly. The skilled artisan will be able to recognize applications where it is desirable to vary the properties of the CG matrix, and will be able to vary the parameters accordingly. The present invention encompasses such variations in the CG matrix.

Although the research that led to this invention involved CG matrices and silicone outer membranes, the skin regeneration method of this invention is not limited to CG matrices and silicone outer membranes. Subsequent research may reveal other fibrous proteins, polymeric molecules or sintered ceramics which can be used in the present invention. Such lattices and materials are within the scope of this invention.

Once the CG matrix has been prepared, the wound is readied for application of the covering. Areas of skin that have been destroyed or damaged are surgically removed to prevent it from interfering with the healing process. The entire area of dead and damaged skin is excised, so that intact epithelial cells are present at the perimeter of the wound. The CG matrix, with the silicone side away from the wound, is draped across the wound to avoid the entrapment of air pockets between the wound and the matrix. The membrane is sutured or stapled to the wound using conventional techniques and then covered with a bandage.

After application of the CG bi-layer, blood vessels and mesenchymal cells from underlying healthy tissue begin, as described hereinabove, the process of infiltration of the grafted CG matrix. "Infiltration", as defined herein, further refers to allowing a sufficient period of time for this migration of mesenchymal cells and blood vessels. Sufficient time periods are those which permit subsequent application of CEA sheets with nearly complete take rates, as described hereinbelow. A preferred period of time is about ten days, but periods as low as about two to three days can also be used.

Another aspect of the present invention refers the regeneration of skin at a burn or wound site on a human or animal using seeded CG matrices. "Seeded CG matrices" refer to CG matrices into which epidermal or dermal cells harvested from a wound free site on the patient's body surface have been introduced. Each epidermal or dermal cell that survives the seeding process can reproduce and multiply, thereby hastening the formation of a neoepidermis and/or neodermis. Preferred epidermal and dermal cells are keratinocytes and fibroblasts, respectively. Seeded CG matrices are described in U.S. Pat. No. 4,060,081, the teachings of which are incorporated herein by reference in its entirety. Matrices which have been seeded are referred to as "cellular" while unseeded matrices are referred to as "acellular".

Seeded CG matrices may be autologous, i.e. matrices seeded with cells obtained from the human or animal having the burn or wound, or they may be heterologous, i.e. seeded with cells obtained from a donor. In addition, cells being used to seed a CG matrix may undergo genetic manipulation in order to prevent rejection or to change the cell's phenotype in some beneficial manner. Genetic manipulation includes introducing genetic matter into the cells so that the protein gene product or products are expressed in sufficient quantities to cause the desired change in phenotype. An example of suitable genetic matter includes the gene encoding for a growth factor along with the requisite control elements.

Once infiltration has occurred the wound is ready for the application of a CEA sheet onto the CG matrix. The CEA sheet eventually forms a neoepidermis. The CEA sheets are prepared by surgically removing split-thickness skin samples from the patient in an area of the patient's body surface (hereinafter referred to as the "donor site") that is wound free. This procedure can take place prior to, concurrent with or after the application of the CG bilayer to the wound bed. The epidermis is enzymatically and/or mechanically removed from the dermis. The epidermal layer is then mechanically and/or enzymatically separated into small pieces of epidermis and preferably into individual cells. The epidermal cells are then placed in culture media and allowed to reproduce until all available intercellular space has been eliminated and the cells have formed sheets from about one to seven layers thick. Cultured epithelial cells that have reached this stage are said to have "reached confluence". This process takes approximately three weeks. The epithelial cells may be subcultured a number of times to produce additional cultured grafts. Subculture takes a primary CEA, separates and resuspends individual cells to be recultured. This can allow for increases of up to four orders of magnitude in areas which can be covered by cultured grafts. A specific procedure for preparing CEA is included in the Exemplification. Preparations of CEA are well known in the art, and the skilled practitioner will know of many variations of the specific procedure disclosed in the Exemplification. In addition, there may be certain applications of this invention where variations in the method of preparing CEA will lead to more desirable results. The skilled artisan will be able to recognize these applications and make the appropriate changes. All such variations in the preparation of CEA that can be used in conjunction with CG matrix to form an artificial skin bilayer are within the scope of this invention. See Teppe, Roberto George Casper, "Cultured Kerotinocyte Grafting: Implications for Wound Healing," Profschrift, Denhang, Netherlands, 1993, the teachings of which are hereby incorporated by references in their entirety.

After CEA sheets have reached confluence, grafting onto the CG matrix can be performed. The moisture barrier (e.g. silicone outer layer) is manually removed from the CG matrix. The surface layer of vascularized matrix may be excised with a dermatome or surgical blade. Hemostasis is achieved with electrocautery, direct pressure or topical hemostatic agents, if desired.

The CEA sheets are removed from the culture flask. Petroleum impregnated gauze is secured to the surface of the sheets with surgical clips. The sheets are then placed on the matrix sites with the basal cell layer side down and secured to the matrix site with sutures or surgical staples, thereby keeping the CEA sheet firmly adherent to the matrix site. The wound is covered with dry sterile gauze which is changed periodically and the CEA is allowed to adhere. An autograft that "takes" is indicated by visually observing epidermis on the wound surface which persists for several days post-grafting. The extent to which a graft takes can be more precisely determined by the amounts of wound surface area which is epithelized, i.e., how much of the wound surface area is covered by neoepidermis. This can be determined by histological means and is described more fully in the Exemplification. A graft which takes is typically characterized by the pressure of epithelial cells covering the neodermis. Eventually there is a formation of a basement membrane at the junction of the neoepidermis and dermis, including components such as anchoring fibrils. This results in a tight union between the neoepidermis and neodermis.

The invention will now be further and specifically described by the following examples.

EXEMPLIFICATION

The effectiveness of the present method of skin regeneration was tested on Yorkshire pigs by applying CEA sheets to four different types of wounds. In one type of wound a CEA sheet was applied onto a CG substrate. A CEA sheet was also applied directly to full thickness wounds freshly excised to subcutaneous fat and to full thickness wounds freshly excised to fascia. Excising a wound to fascia refers to a wound in which the epidermis, dermis and subcutaneous fat layers have all been removed. The ability of the CEA sheets to take to these three types of wounds was tested on three animals, each of which had all three types of wounds. In the fourth wound type, CEA sheets were applied directly to a wound seven days after the wound was created by excising to subcutaneous fat. This type of wound, referred to as "granulating", was tested on two separate animals which were free from the other wound types.

Split thickness skin samples were harvested from three Yorkshire pigs according to the technique described below. The skin samples from each pig were then cultured separately to prepare CEA sheets according to the procedure described below. Fourteen days after the harvesting of the split-thickness skin samples, 4×4 cm full thickness wounds excised to fat using a surgical scalpel were made on the dorsums of the three pigs. A total of sixteen wounds were made on all three pigs. CG bilayers, prepared according to the procedure described below, were applied to the freshly excised wounds, silicone side up. The membrane was then secured with sutures.

Twenty-four days after the taking of the split thickness skin samples, the CEA sheets had reached confluence and were ready for application to the animals' wounds. In preparation for the CEA grafting, the silicone layer on the CG matrices that had been grafted onto the wounds of the subject pigs was manually removed. A total of twelve 4×4 cm full thickness wounds, using standard surgical techniques, were then made on the dorsums of the subject pigs. Eight of these wounds were excised to subcutaneous fat, the other four were excised to faschia.

The CEA sheets prepared from skin harvested from the subject pigs were removed from culture and secured to petroleum impregnated gauze with surgical clips. They were cut to a suitable size and then applied directly to the three types of wounds, basal side down. Each animal was grafted only with CEA sheets derived from cells harvested from that particular animal. Dry sterile gauze was placed over the sheet and secured to the matrix or wound with sutures or stainless steel staples. Dry sterile gauze dressings were applied and changed daily.

Seven days after the grafting of the CEA sheets, the animals were examined for the completeness of graft take. This was first done visually. Areas of CEA that appeared pink, with a translucent surface, were judged to have taken. How completely the grafts had taken was also determined by quantitative histology. Regularly spaced biopsies were taken from each wound. The biopsies were spaced so as to be representative of the wound area. The neoepidermal was examined along the entire cross section of each wound biopsy. Hematoxylin and eosin sections were analyzed along the entire cross section for the presence of epithelial cells on the neodermal surface. The percentage of epithelial coverage on the dermal layer is the histological take. The gross and histological takes are given below in the Table.

The experimental protocol for determining the effectiveness of CEA take when CEA sheets are applied to granulating wounds was the same as described hereinabove except for the following modification. Four full thickness wounds 4×4 cm in size were excised to subcutaneous fat on the dorsum of each animal seventeen days after harvesting the split thickness skin samples and allowed to granulate. Granulating wounds underwent periodic dressing changes with a petroleum impregnated gauze. Grafting of the CEA sheets took place seven days later.

HARVESTING OF SKIN

A fasted Yorkshire pig (15–20 kg) is suspended in a Panepinto body sling and anesthetized with 1.0–2.5% Halothane delivered in conjunction with a 30:50 mixture of nitrous oxide and oxygen via a facial mask. A pulseoxymeter is used to monitor heart rate and blood oxygen levels during the procedure.

The dorsal hair of the scapular area is clipped with shears and the remaining stubble is removed with shaving cream and a razor. The area is then washed for three minutes with germicidal soap and sterile water. A three minute application of 70% isopropanol completes the surface preparation.

The donor area is then sterile draped and sterile mineral oil is used for lubrication. A Goulian knife with a 0.010" shim is used to remove strips of donor skin. The harvested skin is then placed in sterile vials of phosphate buffered saline (PBS) supplemented with an antibiotic/antimycotic solution for travel to the culture facility.

PREPARATION OF CEA

The skin samples are washed twice in fresh PBS, placed in 0.25% dispase solution (single layer with no folds or overlap) and either placed at 37° C. for two hours of 4° C. over night.

After dispasing, the skin samples are again washed in PBS and the epidermis is mechanically separated from the dermis (with a pair of dissecting forceps) and placed in a 0.5%/0.01% solution of trypsin and EDTA. The dermis is scraped with a scalpel to remove any basal cells and then discarded. The epidermal sheets are placed in a single layer without overlap; the sheets are then incubated with the trypsin solution for 30 minutes to separate the cells.

The epidermal samples are finely shredded with forceps and the cell solution is resuspended for one minute. The trypsin activity is neutralized by adding an equivalent amount of fetal bovine serum (FBS) supplemented medium (all references to medium refer to 20% FBS supplemented Waymouth's medium, see below). The cell solution is resuspended for four minutes and filtered through a 100 µm sieve into a new dish. The original dish is washed with 5 ml of medium and filtered to reduce the cell loss during dish transfer. The suspension is placed in a sterile centrifuge tube and centrifuged for five minutes at 1200 rpm (5° C.); the dish can again be rinsed with 5 ml of medium to dislodge extra cells.

After centrifuging, the supernatant is removed, the pellet is re-suspended in 10 ml of medium, and the cell suspension is placed on ice. The cells are counted; trypan blue is used to exclude nonviable cells.

The suspension is then diluted to $1 \times 10^6$ cells/ml and 10 ml of the solution is plated in 75 cm$^2$ culture flasks. The flasks are placed in an incubator (37° C.) with 5% $CO_2$ and 90% humidity. Culture medium is changed every other day. Toward the end of the culture period (approximately three weeks), the medium may need changing daily.

CULTURE MEDIUM WITH SUPPLEMENTS 500 ml 1x Waymouth's Medium MB 752/1

114 ml Fetal Bovine Serum (Sigma F-2442)

5 ml 100x MEM Nonessential Amino Acids 2 ml L-arginine Stock (11.4 g/100 ml)

1 ml Sodium Pyruvate (11.0 g/100 ml)

1 ml Putrescine —HCl Stock (116.11 mg/100 ml)

2 ml Insulin (2.5 mg/ml in 4 mM HCl)

1 ml Hydrocortisone (5 mg/ml in 95% EtOH)

10 µl Cholera Toxin (5 mM)

10 ml 100x Antibiotic/Antimycotic (GIBCO) Amphotericin B (25 ug/ml), Penicillin G Sodium (10000 units/ml), Streptomycin Sulfate (10000 ug/ml).

PREPARATION OF CG MATRIX

Bovine hide collagen, 0.5% by weight is dispersed in 0.05M acetic acid and coprecipitate is concentrated by centrifugation and excess acetic acid is decanted. The concentrated coprecipitate is poured into flat stainless steel freezing pans to a volume of 0.3 ml per square centimeter and placed on the cooled (−30° C.) shelf of a freeze-drier. The frozen aqueous component of the coprecipitate is sublimated under vacuum to produce a highly porous matrix 2–3 mm thick. The constituent molecules of the matrix are cross-linked using a 24 hour dehydrothermal treatment at 105° C. and 30 milliTorr. The now sterile material is coated with a thin (approximately 0.3 mm thick) layer of silicone, which is cured in 0.05M acetic acid at room temperature for 24 hours. The matrix is further cross-linked by a 24 hour treatment with a 0.25% (by volume) glutaraldehyde solution in 0.05M acetic acid. The ECM analog is then exhaustively dialyzed in sterile, de-ionized water and stored in sterile 70% isopropanol until use. Before grafting, the matrix is rinsed in phosphate buffered saline (PBS) to remove the alcohol.

Results

TABLE

|  | Treatment | Gross Take(%) | Histologic Take (%) |
|---|---|---|---|
| Type I | CEA on CG | 100 (n = 16) | 97 ± 3 (n = 2) |
| Type II | CEA on fascia | 0 (n = 4) | 0 (n = 1) |
| Type III | CEA on fat | 0 (n = 8) | 8 (n = 1) |
| Type IV | CEA on granulating wounds |  | 77 ± 10 (n = 8) | n = number of wounds

Gross observations showed complete take of CEA on CG substrate. Histological measurements from 2 sites confirmed that the CEA was 97±3% adherent to the CG substrate, by 7 days after grafting. By contrast, gross observation indicated no take of CEA on fascia or fat. This was confirmed by an observed histologic take on fat and fascia of 8% and 0%, respectively, by 7 days after grafting. Histological observation indicates that CEA take on granulating wounds (77%±10) was better than with CEA on freshly excised wounds, but still inferior to CEA take on CG matrix. The ability of CEA to take when applied directly to granulating wounds has little relevance clinically. A patient suffering from burns or wounds that cover a large portion of the patient's body surface is faced with an immediate threat of a loss of body fluids and infection. Consequently, such a patient cannot afford to wait seven days for a wound to granulate before closing the wound. Therefore, the improvement represented by the present method over existing methods in a clinically relevant setting is determined by comparing the take rates of CEA on CG matrix with the take rates of CEA on freshly excised wounds. These results indicate that the claimed invention represents a clear improvement over existing methods of regenerating skin at wound sites.

Growth, maturation and differentiation of the CEA on CG were histologically similar to that of normal epidermis. CEA grafted on CG matrix, as compared to on full-thickness wounds, appeared less fragile and seems more resistant to shearing. As early as 7 days after grafting CEA onto CG matrix, the resulting tissue was pink, soft and supple.

EQUIVALENTS

Those skilled in the art will know, or be able to ascertain using no more than routine experimentation, many equivalents to the specific embodiments of the invention described herein. These and all other equivalents are intended to be encompassed by the following claims.

The invention claimed is:

1. A method for regenerating skin at a burn or wound site in a human or animal, comprising the steps of:
   a) applying to a wound or burn a synthetic bilayer having a biodegradable porous lattice that is covered with an outer membrane that is a moisture barrier to the wound or burn, wherein:
      i) the porous lattice is applied directly to the wound or burn;
      ii) the moisture barrier is exposed to the air; and
      iii) the synthetic bilayer contains genetically modified autologous or heterologous cells that have been introduced into the synthetic bilayer prior to the grafting onto the burn or wound;
   b) allowing the porous lattice to be infiltrated by blood vessels and mesenchymal cells from healthy tissue under the burn or wound site;
   c) removing the moisture barrier and grafting with a cultured epithelial autograft (CEA) sheet that has reached confluence, wherein the basal cell layer is in contact with the porous lattice, whereby over time a neodermis and neoepidermis are formed at the burn or wound site, resulting in tissue that have the appearance, growth and differentiation similar to normal skin.

2. The method of claim 1, wherein the bilayer membrane comprises a collagen-glycosaminoglycan matrix (CG) and a silicone elastomer outer moisture barrier.

3. The method of claim 2 wherein the cultured epithelial autograft is prepared by the method comprising the steps of:
   a) harvesting split-thickness skin biopsies from an area of the human's or animal's body surface that is free of wounds;
   b) separating the epidermis from the dermis in the harvested split-thickness skin biopsies;
   c) growing the separated epidermal cells in culture until they have reached confluence.

4. The method of claim 3, wherein the harvesting of the split-thickness skin biopsies is performed concurrently with the grafting of the CG matrix.

5. The method of claim 3, wherein the harvesting of the split-thickness skin biopsies are performed prior to the grafting of the CG matrix.

6. The method of claim 3, wherein the harvesting of the split-thickness skin biopsies are performed after the grafting the CG matrix.

7. The method of claim 3 wherein the cells that have been introduced into the synthetic bilayer prior to the grafting onto the burn or wound are autologous.

* * * * *